(12) United States Patent
Anderskewitz et al.

(10) Patent No.: US 7,723,360 B2
(45) Date of Patent: May 25, 2010

(54) ALKYL-AND PIPERIDINE-SUBSTITUTED BENZIMIDAZOLE DERIVATIVES

(75) Inventors: Ralf Anderskewitz, Laupheim (DE); Domnic Martyres, Biberach (DE); Franz Birke, Waldalgesheim (DE); Thierry Bouyssou, Mietingen (DE)

(73) Assignee: Boehringer Ingelheim International GmbH, Ingelheim am Rhein (DE)

( * ) Notice: Subject to any disclaimer, the term of this patent is extended or adjusted under 35 U.S.C. 154(b) by 951 days.

(21) Appl. No.: 11/191,539

(22) Filed: Jul. 28, 2005

(65) Prior Publication Data

US 2006/0030590 A1 Feb. 9, 2006

(30) Foreign Application Priority Data

Aug. 6, 2004 (EP) .................................. 04018690

(51) Int. Cl.
*A61K 31/454* (2006.01)
*C07D 403/02* (2006.01)

(52) U.S. Cl. ....................................... 514/322; 546/199
(58) Field of Classification Search ................. 514/322; 546/199
See application file for complete search history.

(56) References Cited

U.S. PATENT DOCUMENTS

2007/0004736 A1* 1/2007 Kubo et al. .................. 514/249

OTHER PUBLICATIONS

Sato et al. "Psychotropic agents . . . " CA 89:208915 (1978).*
Tsushima et al. "preparation of phenoxy . . . " CA 135:195564 (2001).*
Bryans et al. "triazole derivatives . . . " CA 145:455021 (2006).*
Kubo et al. "imidazole derivative . . . " Ca 141:38631 (2004).*
Bennett Chemical dictionary p. 73-74 (1976).*

* cited by examiner

*Primary Examiner*—Celia Chang
(74) *Attorney, Agent, or Firm*—Michael P. Morris; Mary-Ellen M. Devlin; Timothy X. Witkowski

(57) ABSTRACT

A compound of general formula 1a

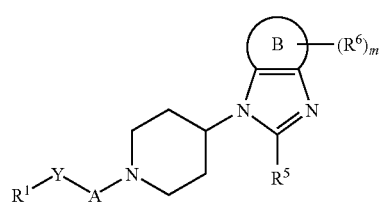

wherein $R^1$, $R^5$, $R^6$, A, B, Y, i, j and m are defined as in the description and claims.

It is another object of the present invention to provide pharmaceutical compositions comprising a pharmaceutically acceptable carrier and a therapeutically effective amount of at least one of the compounds of the present invention or a pharmaceutically acceptable salt thereof.

8 Claims, No Drawings

ALKYL-AND PIPERIDINE-SUBSTITUTED BENZIMIDAZOLE DERIVATIVES

BACKGROUND OF THE INVENTION

1. Technical Field

This invention relates generally to novel benzimidazole-derivatives and their use as modulators of chemokine receptor activity, pharmaceutical compositions containing the same, and methods of using the same as agents for treatment and prevention of inflammatory diseases such as asthma and allergic diseases, as well as autoimmune pathologies such as rheumatoid arthritis and atherosclerosis.

2. Background Information

Chemokines are chemotactic cytokines, of molecular weight 6-15 kDa, that are released by a wide variety of cells to attract and activate, among other cell types, macrophages, T and B lymphocytes, eosinophils, basophils and neutrophils (reviewed in Luster, New Eng. J Med., 338, 436-445 (1998) and Rollins, Blood, 90, 909-928 (1997)).

There are two major classes of chemokines, CXC and CC, depending on whether the first two cysteines in the amino acid sequence are separated by a single amino acid (CXC) or are adjacent (CC). The CXC chemokines, such as interleukin-8 (IL-8), neutrophil-activating protein-2 (NAP2) and melanoma growth stimulatory activity protein (MGSA) are chemotactic primarily for neutrophils and T lymphocytes, whereas the CC chemokines, such as RANTES, MIP-1a, MIP-1 (3, the monocyte chemotactic proteins (MCP-1, MCP-2, MCP-3, MCP-4, and MCP-5) and the eotaxins (-1, -2, and -3) are chemotactic for, among other cell types, macrophages, T lymphocytes, eosinophils, dendritic cells, and basophils. There also exist the chemokines lymphotactin-1, lymphotactin-2 (both C chemokines), and fractalkine (a CXXXC chemokine) that do not fall into either of the major chemokine subfamilies.

The chemokines bind to specific cell-surface receptors belonging to the family of G-protein-coupled seventransmembrane-domain proteins (reviewed in Horuk, Trends Pharm. Sci., 15, 159-165 (1994)) which are termed "chemokine receptors." On binding their cognate ligands, chemokine receptors transduce an intracellular signal through the associated trimeric G proteins, resulting in, among other responses, a rapid increase in intracellular calcium concentration, changes in cell shape, increased expression of cellular adhesion molecules, degranulation, and promotion of cell migration. There are at least ten human chemokine receptors that bind or respond to CC chemokines with the following characteristic patterns: CCR1 (or "CKR-1" or "CC-CKR-1") [MIP-1a, MCP-3, MCP-4, RANTES] (Ben-Barruch, et al., Cell, 72, 415-425 (1993), Luster, New Eng. J. Med., 338, 436-445 (1998)); CCR-2A and CCR-2B (or "CKR-2A"/"CKR-2B" or "CC-CKR-2A"/"CC-CKR-2B") [MCP-1, MCP2, MCP-3, MCP-4, MCP-5] (Charo et al., Proc. Natl. Acad. Sci. USA, 91, 2752-2756 (1994), Luster, New Eng. J. Med., 338, 436-445 (1998)); CCR-3 (or "CKR-3" or "CC-CKR-3") [eotaxin-1, eotaxin-2, RANTES, MCP-3, MCP-4] (Combadiere, et al., J. Biol. Chem., 270, 16491-16494 (1995), Luster, New Eng. J. Med., 338, 436-445 (1998)); CCR-4 (or "CKR-4" or "CC-CKR-4") [TARC, MIP-1a, RANTES, MCP-1] (Power et al., J. Biol. Chem., 270, 19495-19500 (1995), Luster, New Eng. J. Med., 338, 436-445 (1998)); CCR-5 (or "CKR-5" OR "CCCKR-5") [MIP-1a, RANTES, MIP-1p] (Sanson, et al., Biochemistry, 35, 3362-3367 (1996)); CCR-6 (or "CKR-6" or "CC-CKR-6") [LARC] (Baba et al., J. Biol. Chem., 272, 14893-14898 (1997)); CCR-7 (or "CKR-7" or "CC-CKR-7") [ELC] (Yoshie et al., J. Leukoc. Biol. 62, 634-644 (1997)); CCR-8 (or "CKR-8" or "CC-CKR-8") [1-309, TARC, MIP-1p] (Napolitano et al., J. Immunol., 157, 2759-2763 (1996), Bernardini et al., Eur. J. Immunol., 28, 582-588 (1998)); and CCR-10 (or "CKR-10" or "CC-CKR-10") [MCP-1, MCP-3] (Bonini et al, DNA and Cell Biol., 16, 1249-1256 (1997)).

In addition to the mammalian chemokine receptors, mammalian cytomegaloviruses, herpes viruses and poxviruses have been shown to express, in infected cells, proteins with the binding properties of chemokine receptors (reviewed by Wells and Schwartz, Curr. Opin. Biotech., 8, 741-748 (1997)). Human CC chemokines, such as RANTES and MCP-3, can cause rapid mobilization of calcium via these virally encoded receptors. Receptor expression may be permissive for infection by allowing for the subversion of normal immune system surveillance and response to infection. Additionally, human chemokine receptors, such as CXCR-4, CCR-2, CCR-3, CCR-5 and CCR-8, can act as coreceptors for the infection of mammalian cells by microbes as with, for example, the human immunodeficiency viruses (HIV).

Chemokine receptors have been implicated as being important mediators of inflammatory, infectious, and immunoregulatory disorders and diseases, including asthma and allergic diseases, as well as autoimmune pathologies such as rheumatoid arthritis and atherosclerosis. For example, the chemokine receptor CCR-3 plays a pivotal role in attracting eosinophils to sites of allergic inflammation and in subsequently activating these cells. The chemokine ligands for CCR-3 induce a rapid increase in intracellular calcium concentration, increased expression of cellular adhesion molecules, cellular degranulation, and the promotion of eosinophil migration. Accordingly, agents which modulate chemokine receptors would be useful in such disorders and diseases. In addition, agents which modulate chemokine receptors would also be useful in infectious diseases such as by blocking infection of CCR-3 expressing cells by HIV or in preventing the manipulation of immune cellular responses by viruses such as cytomegaloviruses.

BACKGROUND ART

WO 01 66525 discloses substituted benzimidazoles or benzotriazoles for the modulation of the CCR5 receptor for the treatment i.e. HIV 1, inflammatory or immunoregulatory. One can also find in the description the assumption that the disclosed compounds have potential in the treatment of asthma or COPD.

BRIEF SUMMARY OF THE INVENTION

A compound of general formula 1a

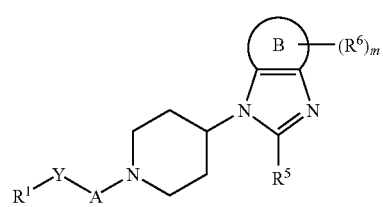

wherein $R^1$, $R^5$, $R^6$, A, B, Y and m are defined as below.

It is another object of the present invention to provide pharmaceutical compositions comprising a pharmaceutically acceptable carrier and a therapeutically effective amount of at least one of the compounds of the present invention or a pharmaceutically acceptable salt thereof. These and other objects, which will become apparent during the following detailed description.

DETAILED DESCRIPTION OF THE INVENTION

The present invention relates to a compound of general formula 1a

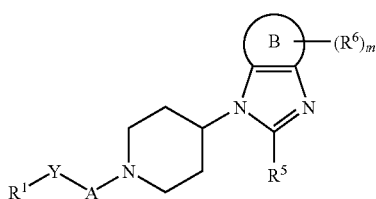

wherein
$R^1$ is aryl, het or a annelated species thereof, wherein het is a heterocyclic ring and the annelated species comprises aryl-het-, het-aryl- or het-het-annelations, each of said aryl or het may be substituted with one, two or three $R^2$;
$R^2$ are each independently —$C_{1-6}$-alkyl, —$C_{3-6}$-cycloalkyl, —$C_{1-6}$-haloalkyl, —$C_{1-6}$-aralkyl, halogen, —CN, —COOR$^3$, —COR$^3$, —CONR$^3$R$^4$, —NR$^3$R$^4$, —NR$^3$COR$^4$, —NR$^3$SO$_2$R$^4$, —OR$^3$, —NO$_2$, —SR$^3$, —SOR$^3$, —SO$_2$R$^3$ or —SO$_2$NR$^3$R$^4$;
$R^3$ is H, —$C_{1-6}$-alkyl;
$R^4$ is H, —$C_{1-6}$-alkyl;
$R^5$ is —$C_{1-6}$-alkyl
$R^6$ are each independently —$C_{1-6}$-alkyl, —$C_{1-6}$-alkoxy, —$C_{1-6}$-acyloxy, —$C_{1-6}$-aralkyl, —$C_{3-6}$-cycloalkyl, —$C_{1-6}$-haloalkyl, —$C_{1-6}$-thioalkyl, halogen, —OR$^3$, —SR$^3$, —CN, —NO$_2$, —COOR$^3$, —COR$^3$, —CONR$^3$R$^4$, —NR$^3$R$^4$, —NR$^3$COR$^4$, —NR$^3$SO$_2$R$^4$, —SOR$^3$, —SO$_2$R$^3$, —SO$_2$NR$^3$R$^4$, aryl or het;
A is —$C_{2-8}$-alkylene, optionally substituted with —$C_{1-3}$-alkyl, halogen or —OH;
B is aryl or het;
Y is —CF$_2$—, —NR$^4$—, —O—, —S(O)$_n$;
n is 0, 1 or 2;
m is 0, 1, 2, 3 or 4;

and pharmaceutically acceptable salts thereof.

The compounds herein described may have asymmetric centres. Compounds of the present invention containing an asymmetrically substituted atom may be isolated in optically active or racemic forms. It is well known in the art how to prepare optically active forms, such as by resolution of racemic forms or by synthesis from optically active starting materials. Many geometric isomers of olefins, C=N double bonds, and the like can also be present in the compounds described herein, and all such stable isomers are contemplated in the present invention. Cis and trans geometric isomers of the compounds of the present invention are described and may be isolated as a mixture of isomers or as separated isomeric forms. All chiral, diastereomeric, racemic forms and all geometric isomeric forms of a structure are intended, unless the specific stereochemistry or isomeric form is specifically indicated.

Used Terms and Definitions

Terms not specifically defined herein should be given the meanings that would be given to them by one of skill in the art in light of the disclosure and the context. As used in the specification, however, unless specified to the contrary, the following terms have the meaning indicated and the following conventions are adhered to. In the groups, radicals, or moieties defined below, the number of carbon atoms is often specified preceding the group, for example, —$C_{1-6}$ alkyl means an alkyl group or radical having 1 to 6 carbon atoms. In general, for groups comprising two or more subgroups, the last named group is the radical attachment point, for example, "thioalkyl" means a monovalent radical of the formula HS-Alk-. Unless otherwise specified below, conventional definitions of terms control and conventional stable atom valences are presumed and achieved in all formulas and groups.

In general, all tautomeric forms and isomeric forms and mixtures, whether individual geometric isomers or optical isomers or racemic or non-racemic mixtures of isomers, of a chemical structure or compound is intended, unless the specific stereochemistry or isomeric form is specifically indicated in the compound name or structure.

The term "substituted" as used herein, means that any one or more hydrogens on the designated atom is replaced with a selection from the indicated group, provided that the designated atom's normal valence is not exceeded, and that the substitution results in a stable compound.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

As used herein, "pharmaceutically acceptable salts" refer to derivatives of the disclosed compounds wherein the parent compound is modified by making acid or base salts thereof. Examples of pharmaceutically acceptable salts include, but are not limited to, mineral or organic acid salts of basic residues such as amines; alkali or organic salts of acidic residues such as carboxylic acids; and the like. The pharmaceutically acceptable salts include the conventional non-toxic salts or the quaternary ammonium salts of the parent compound formed, for example, from non-toxic inorganic or organic acids. For example, such conventional non-toxic salts include those derived from inorganic acids such as hydrochloric, hydrobromic, sulfuric, sulfamic, phosphoric, nitric and the like; and the salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxybenzoic, fumaric, toluenesulfonic, methanesulfonic, ethane disulfonic, oxalic, isethionic, and the like.

The pharmaceutically acceptable salts of the present invention can be synthesized from the parent compound which contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; generally, non-aqueous media like ether, ethyl acetate, ethanol, isopropanol, or acetonitrile are preferred. Lists of suitable salts are found in Remington's Pharmaceutical Sciences, Mack Publishing Company, a standard reference text in this field. which release an active parent drug of the present invention in vivo when such prodrug is administered to a mammalian subject. Prodrugs the present invention are prepared by modifying functional groups present in the compound in such a way that the modifications are cleaved, either in routine manipulation or in vivo, to the parent compound. Prodrugs include compounds of the present invention wherein a hydroxy, amino, or sulfhydryl group is bonded to any group that, when the prodrug of the present invention is administered to a mammalian subject, it cleaves to form a free hydroxyl, free amino, or free sulfhydryl group, respectively. Examples of prodrugs include, but are not limited to, acetate, formate and benzoate derivatives of alcohol and amine functional groups in the compounds of the present invention.

The term "aryl" as used herein, either alone or in combination with another substituent, means either an aromatic monocyclic system or aromatic multicyclic systems containing carbon atoms. For example, aryl includes a phenyl or a naphthyl ring system, wherein aryl means generally an aromatic system, for example phenyl.

The term "het" as used herein, either alone or in combination with another substituent, means a monovalent substituent derived by removal of a hydrogen from a five-, six- or seven-membered saturated or unsaturated (including aromatic) heterocycle containing carbon atoms and one, two, three or four ring heteroatoms selected from nitrogen, oxygen and sulfur. Examples of suitable heterocycles include: tetrahydrofuran, thiophene, diazepine, isoxazole, piperidine, dioxane, morpholine, piperazine or

Although generally covered under the term "het", the term "heteroaryl" as used herein precisely defines an unsaturated heterocycle for which the double bonds form an aromatic system. Suitable example of heteroaromatic system include: pyridine, pyrimidine,

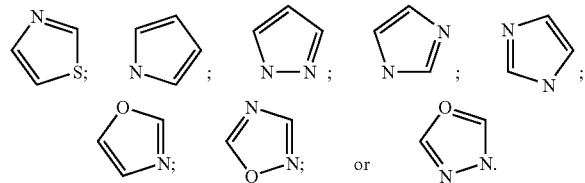

The term "annelated species of aryl or het" as used herein, either alone or in combination with another substituent wherein the annelated species presents as a aryl-het (a), a het-aryl (b) or a het-het (c) annelation means a monovalent substituent derived by removal of one hydrogen from
  a) an aromatic monocyclic system or aromatic multicyclic systems containing carbon atoms, which is annelated to a five-, six- or seven-membered saturated or unsaturated (including aromatic) heterocycle containing carbon atoms and one, two, three or four ring heteroatoms selected from nitrogen, oxygen and sulfur or
  b) a five-, six-, or seven-membered saturated or unsaturated (including aromatic) heterocycle containing carbon atoms and one, two, three or four ring heteroatoms selected from nitrogen, oxygen and sulfur, which is annelated to an aromatic monocyclic system or aromatic multicyclic systems containing carbon atoms or
  c) a five-, six-, or seven-membered saturated or unsaturated (including aromatic) heterocycle containing carbon atoms and one, two, three or four ring heteroatoms selected from nitrogen, oxygen and sulfur, which is annelated to a five-, six-, or seven-membered saturated or unsaturated (including aromatic) heterocycle containing carbon atoms and one, two, three or four ring heteroatoms selected from nitrogen, oxygen and sulfur.

Suitable examples of an annelated species of aryl or het include: quinolinyl, 1-indoyl, 3-indoyl, 5-indoyl, 6-indoyl, indolizinyl, benzimidazyl or purinyl.

The term "halogen" as used herein means a halogen substituent selected from fluoro, chloro, bromo or iodo.

The term "—$C_{1-6}$-alkyl" as used herein, either alone or in combination with another substituent, means acyclic, straight or branched chain alkyl substituents containing from one to six carbon atoms and includes, for example, methyl, ethyl, propyl, butyl, hexyl, 1-methylethyl, 1-methylpropyl, 2-methylpropyl or 1,1-dimethylethyl.

The term "—$C_{3-8}$-cycloalkyl" as used herein, either alone or in combination with another substituent, means a cycloalkyl substituent containing from three to six carbon atoms and includes cyclopropyl, cyclobutyl, cyclopentyl or cyclohexyl.

The term "—$C_{1-6}$-haloalkyl" as used herein, either alone or in combination with another substituent, means acyclic, straight or branched chain alkyl substituents containing up to six carbon atoms having one or more hydrogens substituted for a halogen selected from bromo, chloro, fluoro or iodo. Accordingly "—$C_{2-6}$-haloalkyl" has the same meaning with exception that the chain contains two to six carbon atoms. Preferably the term —$C_{1-6}$-haloalkyl represents —$C_{1-6}$-fluoroalkyl such as 2-fluoroethyl, 2,2,2-trifluorethyl or perfluorethyl.

The term "—$C_{1-6}$-alkoxy" as used herein, either alone or in combination with another substituent, means the substituent —$C_{1-6}$-alkyl-O— wherein alkyl is as defined above containing up to six carbon atoms. Alkoxy includes methoxy, ethoxy, propoxy, 1-methylethoxy, butoxy or 1,1-dimethylethoxy. The latter substituent is known commonly as t-butoxy.

The term "—$C_{1-6}$-acyloxy" as used herein, either alone or in combination with another substituent, means the substituent —$C_{1-6}$-alkyl-(CO)O— wherein alkyl is as defined above containing up to six carbon atoms. Acyloxy includes MeCOO—, EtCOO—, $^n$PrCOO—, $^i$PrCOO—, $^n$BuCOO—, $^{sec}$BuCOO— or $^{tert}$BuCOO—.

The term "—$C_{1-6}$-aralkyl" as used herein, either alone or in combination with another substituent, means the substituent -Aryl-$C_{1-6}$-alkyl- wherein alkyl is as defined above containing up to six carbon atoms. Aralkyl includes benzyl, phenylethyl, phenylpropyl, 1-phenyl-1-methylethyl, phenylbutyl or 1-phenyl-1,1-dimethylethoxy.

—$C_{1-6}$-thioalkyl The term "—$C_{1-6}$-thioalkyl" as used herein, either alone or in combination with another substituent, means acyclic, straight or branched chain alkyl substituents containing up to six carbon atoms and a thiol (HS) group as a substituent. An example of a thioalkyl group is a thiopropyl, e.g., HS—$CH_2CH_2CH_2$—.

The term "—$C_{2-8}$-alkylene" as used herein means a divalent alkyl substituent derived by the removal of one hydrogen atom from each end of a saturated straight or branched chain aliphatic hydrocarbon containing from two to eight carbon atoms and includes, for example, CH₂CH₂C(CH₃)₂CH₂CH₂—. Accordingly "—$C_{1-3}$-alkylene" has the same meaning with exception that the chain contains one to three carbon atoms.

PREFERRED EMBODIMENTS

The compounds of the instant application are useful for manufacturing a medicament for the prevention and/or treatment of diseases wherein the activity of a CCR-3-receptor is involved.

Preferred is the manufacturing of a medicament for treatment of a wide variety of inflammatory, infectious, and immunoregulatory disorders and diseases, including asthma and allergic diseases, infection by pathogenic microbes (which, by definition, includes viruses), as well as autoimmune pathologies such as the rheumatoid arthritis and atherosclerosis.

Most preferred is the manufacturing of a medicament for the treatment of e.g. inflammatory or allergic diseases and conditions, including respiratory allergic diseases such as asthma, allergic rhinitis, hypersensitivity lung diseases, hypersensitivity pneumonitis, eosinophilic cellulitis (e.g., Well's syndrome), eosinophilic pneumonias (e.g., Loeffler's syndrome, chronic eosinophilic pneumonia), eosinophilic fasciitis (e.g., Shulman's syndrome), delayed-type hypersensitivity, interstitial lung diseases (ILD) (e.g., idiopathic pulmonary fibrosis, or ILD associated with rheumatoid arthritis, systemic lupus erythematosus, ankylosing spondylitis, systemic sclerosis, Sjogren's syndrome, polymyositis or dermatomyositis); systemic anaphylaxis or hypersensitivity responses, drug allergies (e.g., to penicillin, cephalosporins), eosinophilia-myalgia syndrome due to the ingestion of contaminated tryptophan, insect sting allergies; autoimmune diseases, such as rheumatoid arthritis, psoriatic arthritis, multiple sclerosis, systemic lupus erythematosus, myasthenia gravis, juvenile onset diabetes; glomerulonephritis, autoimmune thyroiditis, Behcet's disease; graft rejection (e.g., in transplantation), including allograft rejection or graftversus-host disease; inflammatory bowel diseases, such as Crohn's disease and ulcerative colitis; spondyloarthropathies; scleroderma; psoriasis (including Tcell mediated psoriasis) and inflammatory dermatoses such as an dermatitis, eczema, atopic dermatitis, allergic contact dermatitis, urticaria; vasculitis (e.g., necrotizing, cutaneous, and hypersensitivity vasculitis); eosinophilic myositis, eosinophilic fasciitis; cancers with leukocyte infiltration of the skin or organs.

Preferred are compounds of the general formula 1a wherein:
$R^1$ is aryl or het, each optionally substituted with one, two or three $R^2$;
$R^2$ are each independently —$C_{1-6}$-alkyl, —$C_{1-6}$-haloalkyl, halogen, —CN, —$OR^3$ or —$NO_2$;
$R^3$ is H or Methyl;
$R^5$ is —$C_{1-6}$-alkyl
$R^6$ are each independently —$C_{1-6}$-alkyl, —$C_{1-6}$-alkoxy, —$C_{1-6}$-haloalkyl, halogen, —$OR^3$, —CN or —$NO_2$;
A is —$C_{2-8}$-alkylene;
B is aryl;
Y is —NH—, —O—, —$S(O)_n$—;
n is 0 or 2;
m is 0, 1 or 2;

and pharmaceutically acceptable salts thereof.

Particularly preferred are compounds of general formula 1b, wherein $R^1$, $R^5$, $R^6$, A, B, Y and m are defined as above.

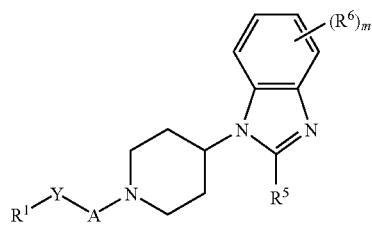

1b and pharmaceutically acceptable salts thereof. Most preferred are compounds of general formula 1c,

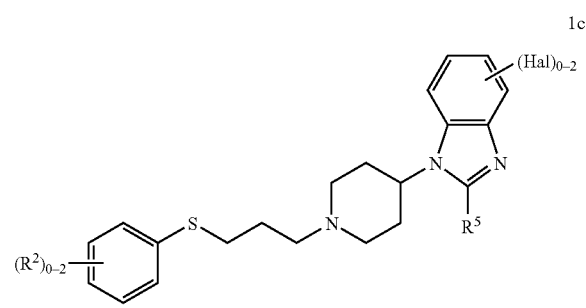

1c wherein $R^5$ is defined as above and
$R^2$ is —$CF_3$ or halogen;
Hal is halogen and pharmaceutically acceptable salts thereof.

Most preferred are compounds of the general formula 1a, 1b or 1c wherein:
$R^1$ is aryl, both optionally substituted with one, two or three $R^2$; more preferred $R^1$ is phenyl, optionally substituted with one, two or three $R^2$, or
$R^2$ is —$CF_3$ or halogen, in particular fluoro; or
—$R^6$ is preferably halogen, in particular fluoro; or
A is —$C_{2-8}$-alkylene or more preferred —CH₂—CH₂—CH₂—; or
B is phenyl: or
Y is —NH—, —O—, —S—, —$SO_2$—;
m is 1 or 2;

and pharmaceutically acceptable salts thereof.

Particular preferred are compounds of the general formula 1c wherein
$R^2$ is fluoro;
$R^5$ is —$C_{1-6}$-alkyl, preferably Methyl, Ethyl, Propyl and Butyl, more preferably Ethyl and Propyl;
Hal is fluoro or chloro;

and pharmaceutically acceptable salts thereof.

Most preferred is a compound of formula 1d

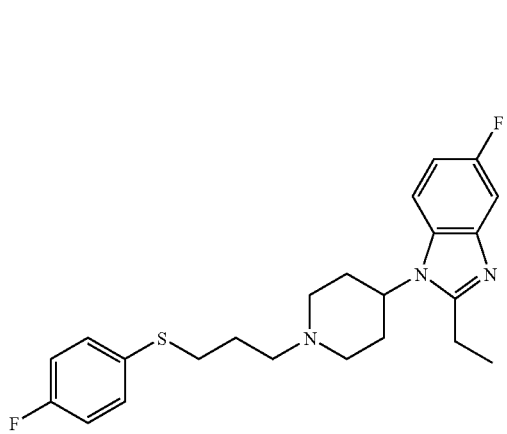

1d and pharmaceutically acceptable salts thereof.

The compounds of formula 1a, 1b, 1c or 1d can be prepared using the reactions and techniques described below. The reactions are performed in a solvent appropriate to the reagents and materials employed and suitable for the transformations being effected. It will be understood by those skilled in the art of organic synthesis that the functionality present on the molecule should be consistent with the transformations proposed. This will sometimes require a judgment to modify the order of the synthetic steps or to select one particular process scheme over another in order to obtain a desired compound of the invention. It will also be recognized that another major consideration in the planning of any synthetic route in this field is the judicious choice of the protecting group used for protection of the reactive functional groups present in the compounds described in this invention. An authoritative account describing the many alternatives to the trained practitioner is Greene and Wuts (Protective Groups In Organic Synthesis, Wiley and Sons, 1991).

Preparation

Compounds of the general formula 1a are prepared by adding a ring B, substituted at least by one nitro-function and a suitable leaving group (LG=i.e. F, Cl) in ortho-position.

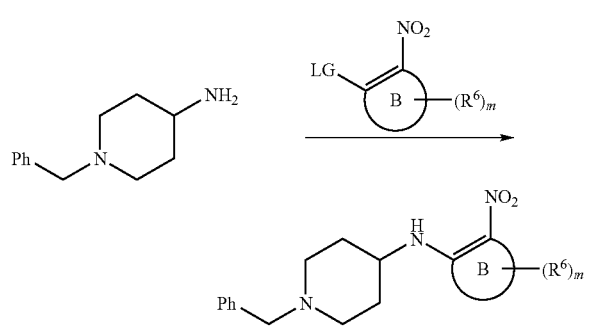

After coupling reaction, the nitro function is reduced by e.g. Hydrogen in presence of a Platinum/Charcoal catalyst, Fe/HCl, SnCl$_2$ or Sodiumdithionite (Na$_2$S$_2$O$_4$) to a free amine group.

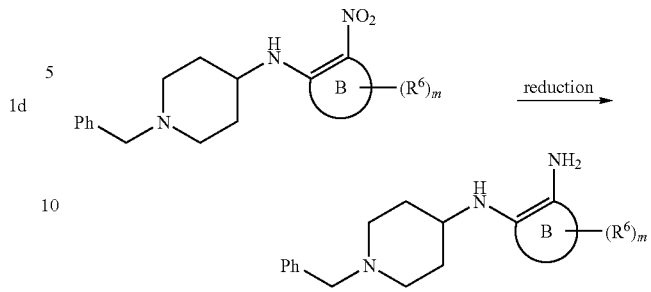

In the next step of the reaction, the resulting amine function is converted into an amide group and thereafter in the same or a separate step transformed in a ring-closing reaction to an imidazole derivative.

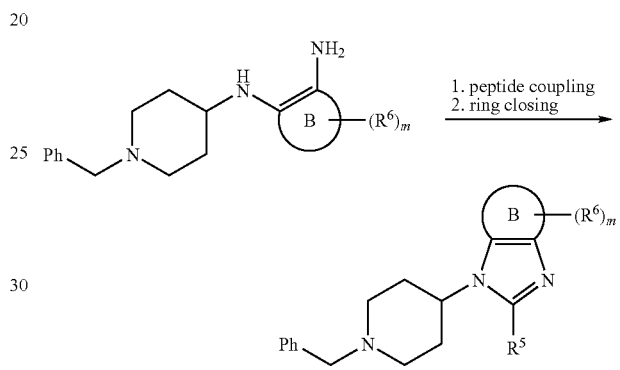

wherein the whole process R$^5$, R$^6$, B, W, i, j, k, l and m are defined as above.

After this, the protecting benzyl group of the piperidine is removed and preferably, the compounds of general formula 1a are prepared by reaction of a compound of general formula 2

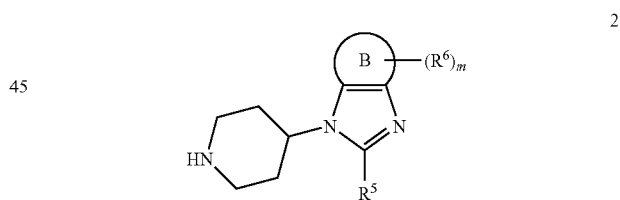

with a compound of the general formula 3.

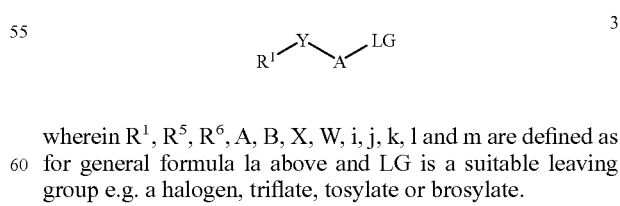

wherein R$^1$, R$^5$, R$^6$, A, B, X, W, i, j, k, l and m are defined as for general formula 1a above and LG is a suitable leaving group e.g. a halogen, triflate, tosylate or brosylate.

As will be appreciated by one of skill in the art, numerous modifications and variations of the present invention are possible in light of the above teachings. It is therefore to be understood that within the scope of the appended claims, the invention may be practiced otherwise than as specifically described herein.

Example 1

1-Benzyl-4-(4-fluoro-2-nitro-phenylamino)-piperidine

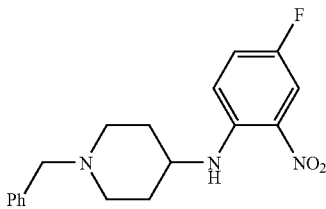

2,5-Difluoro-nitrobenzene (21.5 g), 1-benzyl-4-amino-piperidine (52.3 g) and N-methyl-piperidone (100 ml) were stirred at 100° C. for 3 h. After cooling the mixture was partitioned between water and ethyl acetate and the aqueous layer was extracted twice with ethyl acetate. The combined organic layers were extracted 5 times with water, and the solvent was evaporated in vacuo. The target compound was crystallized from methanol to yield 38.7 g of the title compound as orange crystals (mp. 86-87° C.).

Example 2

1-Benzyl-4-(2-amino-4-fluorophenylamino)-piperidine

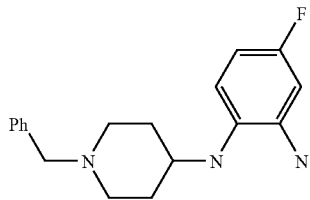

1-Benzyl-4-(4-fluoro-2-nitrophenylamino)-piperidine (10.1 g) were dissolved in 1:1 THF-methanol (150 ml) and hydrogenated with Pt/C (1.5 g, 10%) at room temperature for 1.5 h. The catalyst was then removed by filtration, and the filtrate evaporated to yield 9.1 g of the title compound as an oil. The compound was used without further purification.

Example 3

N-[2-(1-Benzyl-piperidin-4-ylamino)-5-fluorophenyl]-propionamide

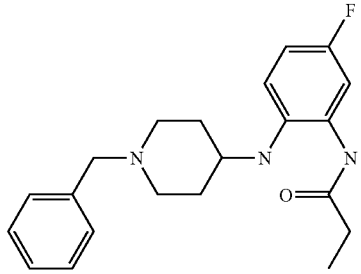

To a stirred solution of 1-Benzyl-4-(2-amino-4-fluorophenylamino)-piperidine (6 g) in ethyl acetate (50 ml) at room temperature was added acetic anhydride (3.3 ml). After 2 h, the reaction was concentrated in vacuo, and the crude oil partitioned between 2:1 DCM and water (150 ml) which was made alkaline with NaOH(aq). The organic layer was separated, washed with water and dried followed by in vacuo concentration to yield 7 g of the title compound as a yellow oil. The compound was used without further purification.

Example 4

1-(1-Benzyl-piperidin-4-yl)-2-ethyl-5-fluoro-1H-benzimidazole

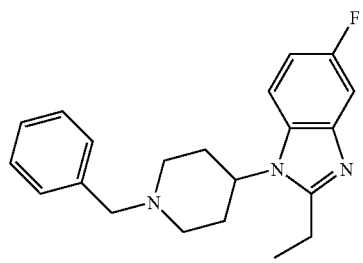

N-[2-(1-Benzyl-piperidin-4-ylamino)-5-fluorophenyl]-propionamide (7 g) in glacial acetic acid (70 ml) was heated at reflux for 1 h. After cooling the residue was dissolved in ethyl acetate (100 ml) and water (50 ml) was then added. The mixture was made alkaline with K2CO3, and the organic layer separated, washed with water, then dried and concentrated in vacuo. The resulting oil was purified by flash chromatography (9:1 DCM:MeOH) to yield 6.4 g of the title compound.

Example 5

2-Ethyl-5-fluoro-1-piperidin-4-yl-1H-benzimidazole

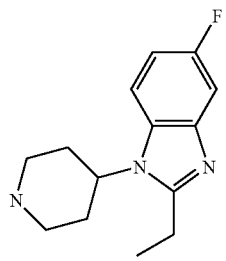

1-(1-Benzyl-piperidin-4-yl)-2-ethyl-5-fluoro-1H-benzimidazole (6.4 g) in methanol (100 ml) was hydrogenated with Pd/C (10%, 1.5 g) at room temperature for 8 h. The catalyst was removed and the filtrate was evaporated and dissolved in ethanol. The solution was acidified with conc. HCl(aq) and recrystallised by the addition of acetone. This yielded 5.3 g of the title compound as colourless crystals.

$^1$H-NMR (DMSO-$d_6$) δ [ppm]=1.40 (3H), 2.09-2.15 (2H), 2.81-2.94 (2H), 3.10-3.22 (2H), 3.22-3.29 (2H), 3.41-3.51 (2H), 4.99-5.11 (1H), 7.40 (1H), 7.69 (1H), 8.56 (1H), 9.30 (1H), 10.03 (1H).

Example 6

1-(3-Bromo-propylsulfanyl)-4-fluoro-benzene

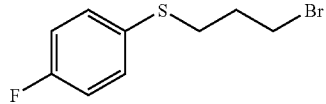

4-Fluorothiophenol (5.3 ml), 1,3-dibromo-propane (15.3 ml), K$_2$CO$_3$ (14 g) were dissolved in CH$_3$CN (100 ml) and refluxed for 3 h. The insoluble salts were removed, the solvent was evaporated and the residue dissolved in ethyl acetate (70 ml). The solution was extracted with diluted NaOH and water, dried and the solvent evaporated in vacuo. The residue was purified by distillation to yield 8 g of the title compound as a colourless oil. Bp. 150-155° C. @ 20 mmHg.

Example 7

2-Ethyl-5-fluoro-1-{1-[3-(4-fluorophenylsulfanyl)-propyl]-piperidin-4-yl}-1H-benzimidazole

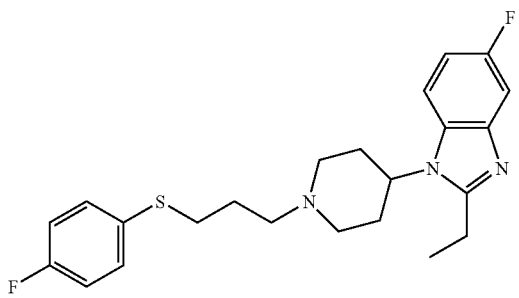

To a solution of 2-Ethyl-5-fluoro-1-piperidin-4-yl-1H-benzimidazole (5.4 g) in DMF (30 ml) was added 1-(3-bromo-propylsulfanyl)-4-fluoro-benzene (5.7 g), K$_2$CO$_3$ (3.2 g) and KI (150 mg). The reaction was stirred at 90° C. for 1 h. After cooling the mixture was poured into water (50 ml) and was extracted with ethyl acetate (2×50 ml). The organic layer was washed with water (2×40 ml), dried and concentrated in vacuo. The resulting oil was purified by flash chromatography (97:3 DCM:MeOH), and the HCl salt (7.5 g) of the title compound obtained by treatment of the purified oil with conc. HCl(aq) in an isopropanol-acetone solvent mixture, followed by recrystallisation from acetone-MeOH. Mp. 252-255° C.

According to the synthetic route above the following examples were prepared:

Example 8

2-Ethyl-1-{1-[3-(4-fluorophenylsulfanyl)-propyl]-piperidin-4-yl}-1H-benzimidazole

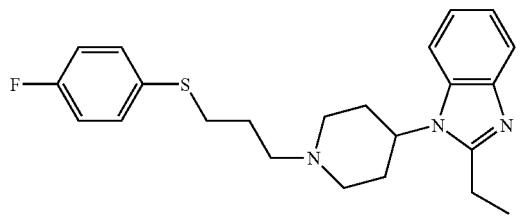

To a stirred solution of 1-(3-bromopropylsulfanyl)-4-fluorobenzene (0.5 g) and 2-ethyl-1-piperidin-4-yl-1H-benzimidazole (0.5 g) in DMF (5 ml) was added K$_2$CO$_3$ (1.0 g) and KI (0.05 g). The mixture was heated at 100° C. for 1 h, and then allowed to cool to rt. Water (50 ml) was added and the mixture extracted with ethyl acetate (80 ml), and the organic layer separated and washed with water. This was further dried and concentrated in vacuo. The oil was purified by flash chromatography (9:1 DCM:MeOH) to yield 0.6 g of the title compound as colourless crystals. Mp. 182-184° C.

Example 9

2-Butyl-1-{1-[3-(4-fluorophenylsulfanyl)-propyl]-piperidin-4-yl}-1H-benzimidazole

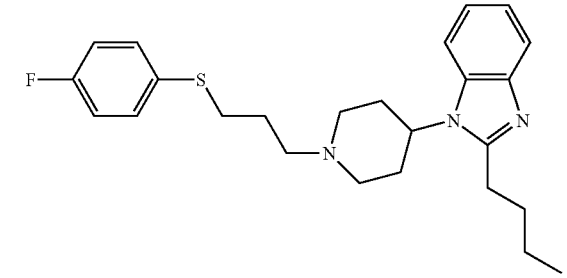

To a stirred solution of 1-(3-bromopropylsulfanyl)-4-fluorobenzene (0.2 g) and 2-butyl-1-piperidin-4-yl-1H-benzimidazole (0.3 g) in DMF (5 ml) was added K$_2$CO$_3$ (0.6 g) and KI (0.05 g). The mixture was heated at 100° C. for 1 h, and then allowed to cool to rt. Water (50 ml) was added and the mixture extracted with ethyl acetate (80 ml), and the organic layer separated and washed with water. This was further dried and concentrated in vacuo. The oil was purified by flash chromatography (9:1 DCM:MeOH) to yield 0.3 g of the title compound as colourless crystals. Mp. 159-161° C.

Example 10

{3-[4-(2-Ethylbenzimidazol-1-yl)-piperidin-1-yl]-propyl}-(4-fluorophenyl)-amine

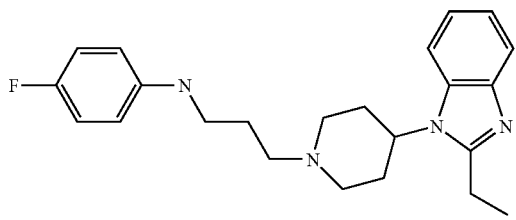

To a stirred solution of 2-ethyl-1-piperidin-4-yl-1H-benzimidazole (0.6 g) and (3-chloropropyl)-(4-fluorophenyl)amine (0.4 g) in DMF (7 ml) was added $K_2CO_3$ (1.1 g) and KI (0.1 g). The mixture was heated at 100° C. for 2 h, and then allowed to cool to rt. Water (50 ml) was added and the mixture extracted with ethyl acetate (80 ml), and the organic layer separated and washed with water. This was further dried and concentrated in vacuo. The oil was purified by flash chromatography (95:5 DCM:MeOH), and the solid recrystallised from ether to yield 0.3 g of the title compound as colourless crystals. Mp. 121-124° C.

Example 11

2-Ethyl-1-{1-[3-(4-fluorobenzenesulfonyl-)propyl]-piperidin-4-yl}-1H-benzimidazole

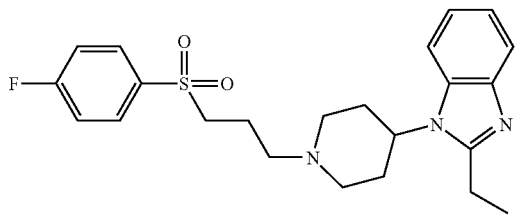

To a stirred solution of 2-ethyl-1-piperidin-4-yl-1H-benzimidazole dihydrochloride (3.02 g) and 1-(3-chloropropane-1-sulfonyl)4-fluorobenzene (2.6 g) in 3:1 THF-DMF (25 ml) was added $NaHCO_3$ (2.9 g), KI (0.3 g) and HMPT (5 ml). The mixture was heated at reflux for 2 h, and then allowed to cool to rt. Water (100 ml) was added and the mixture extracted with ethyl acetate (2×80 ml), and the organic layer separated and washed with water. This was further dried and concentrated in vacuo. The oil was purified by flash chromatography and the free base converted to the hydrochloride salt by action of HCl in ethanol. The solid was recrystallised from ethanol-petroleum ether to yield 2.0 g of the title compound as colourless crystals. Mp. 212-216° C.

Example 12

1-{1-[3-(4-Fluorophenoxy)-propyl]-piperidin-4-yl}-1H-benzimidazole

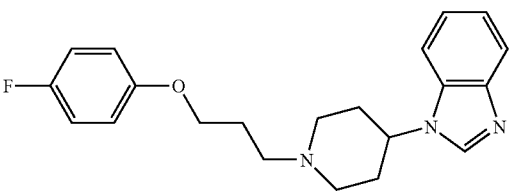

To a stirred solution of 1-piperidin-4-yl-1H-benzimidazole (4.02 g) and 1-(3-chloropropoxy)-4-fluorobenzene (4.16 g) in DMF (50 ml) was added $K_2CO_3$ (4.1 g) and KI (0.2 g). The mixture was heated at 90° C. for 2 h, and then allowed to cool to rt. Water (100 ml) was added and the mixture extracted with ethyl acetate (2×80 ml), and the organic layer separated and washed with water. This was further dried and concentrated in vacuo. The free base converted to the hydrochloride salt by action of HCl in ethanol. The solid was recrystallised from ethanol-diethylether to yield 4.7 g of the title compound as colourless crystals. MP. 233-235° C.

Method of Treatment

Accordingly, the present invention is directed towards compounds which are useful in the prevention and/or treatment of a wide variety of inflammatory, infectious, and immunoregulatory disorders and diseases, including asthma and allergic diseases, infection by pathogenic microbes (which, by definition, includes viruses), as well as autoimmune pathologies such as the rheumatoid arthritis and atherosclerosis.

For example, an instant compound which inhibits one or more functions of a mammalian chemokine receptor (e.g., a human chemokine receptor) may be administered to inhibit (i.e., reduce or prevent) inflammation or infectious disease. As a result, one or more inflammatory process, such as leukocyte emigration, adhesion, chemotaxis, exocytosis (e.g., of enzymes, histamine) or inflammatory mediator release, is inhibited. For example, eosinophilic infiltration to inflammatory sites (e.g., in asthma or allergic rhinitis) can be inhibited according to the present method. In particular, the compound of the following examples has activity in blocking the migration of cells expressing the CCR-3 receptor using the appropriate chemokines in the aforementioned assays.

Similarly, an instant compound which promotes one or more functions of the mammalian chemokine receptor (e.g., a human chemokine) as administered to stimulate (induce or enhance) an immune or inflammatory response, such as leukocyte emigration, adhesion, chemotaxis, exocytosis (e.g., of enzymes, histamine) or inflammatory mediator release, resulting in the beneficial stimulation of inflammatory processes. For example, eosinophils can be recruited to combat parasitic infections. In addition, treatment of the aforementioned inflammatory, allergic and autoimmune diseases can also be contemplated for an instant compound which promotes one or more functions of the mammalian chemokine receptor if one contemplates the delivery of sufficient compound to cause the loss of receptor expression on cells through the induction of chemokine receptor internalization or the delivery of compound in a manner that results in the misdirection of the migration of cells.

In addition to primates, such as humans, a variety of other mammals can be treated according to the method of the present invention. For instance, mammals, including but not limited to, cows, sheep, goats, horses, dogs, cats, guinea pigs, rats or other bovine, ovine, equine, canine, feline, rodent or murine species can be treated. However, the method can also be practiced in other species, such as avian species. The subject treated in the methods above is a mammal, male or female, in whom modulation of chemokine receptor activity is desired. "Modulation" as used herein is intended to encompass antagonism, agonism, partial antagonism and/or partial agonism.

Diseases or conditions of human or other species which can be treated with inhibitors of chemokine receptor function, include, but are not limited to: inflammatory or allergic diseases and conditions, including respiratory allergic diseases such as asthma, allergic rhinitis, hypersensitivity lung diseases, hypersensitivity pneumonitis, eosinophilic cellulitis (e.g., Well's syndrome), eosinophilic pneumonias (e.g., Loeffler's syndrome, chronic eosinophilic pneumonia), eosinophilic fasciitis (e.g., Shulman's syndrome), delayed-type hypersensitivity, interstitial lung diseases (ILD) (e.g., idiopathic pulmonary fibrosis, or ILD associated with rheumatoid arthritis, systemic lupus erythematosus, ankylosing spondylitis, systemic sclerosis, Sjogren's syndrome, polymyositis or dermatomyositis); systemic anaphylaxis or hypersensitivity responses, drug allergies (e.g., to penicillin, cephalosporins), eosinophilia-myalgia syndrome due to the ingestion of contaminated tryptophan, insect sting allergies; autoimmune diseases, such as rheumatoid arthritis, psoriatic arthritis, multiple sclerosis, systemic lupus erythematosus, myasthenia gravis, juvenile onset diabetes; glomerulonephritis, autoimmune thyroiditis, Behcet's disease; graft rejection (e.g., in transplantation), including allograft rejection or graftversus-host disease; inflammatory bowel diseases, such as Crohn's disease and ulcerative colitis; spondyloarthropathies; scleroderma; psoriasis (including Tcell mediated psoriasis) and inflammatory dermatoses such as an dermatitis, eczema, atopic dermatitis, allergic contact dermatitis, urticaria; vasculitis (e.g., necrotizing, cutaneous, and hypersensitivity vasculitis); eosinophilic myositis, eosinophilic fasciitis; cancers with leukocyte infiltration of the skin or organs. Other diseases or conditions in which undesirable inflammatory responses are to be inhibited can be treated, including, but not limited to, reperfusion injury, atherosclerosis, certain hematologic malignancies, cytokine-induced toxicity (e.g., septic shock, endotoxic shock), polymyositis, dermatomyositis. Infectious diseases or conditions of human or other species which can be treated with inhibitors of chemokine receptor function, include, but are not limited to, HIV.

Diseases or conditions of humans or other species which can be treated with promoters of chemokine receptor function, include, but are not limited to: immunosuppression, such as that in individuals with immunodeficiency syndromes such as AIDS or other viral infections, individuals undergoing radiation therapy, chemotherapy, therapy for autoimmune disease or drug therapy (e.g., corticosteroid therapy), which causes immunosuppression; immunosuppression due to congenital deficiency in receptor function or other causes; and infections diseases, such as parasitic diseases, including, but not limited to helminth infections, such as nematodes (round worms); (*Trichuriasis, Enterobiasis, Ascariasis,* Hookworm, *Strongyloidiasis, Trichinosis,* filariasis); trematodes (flukes) (*Schistosomiasis, Clonorchiasis*), cestodes (tape worms) (*Echinococcosis, Taeniasis saginata, Cysticercosis*); visceral worms, visceral larva migraines (e.g., *Toxocara*), eosinophilic gastroenteritis (e.g., *Anisaki* sp., *Phocanema* sp.), cutaneous larva migraines (*Ancylostona braziliense, Ancylostoma caninum*). The compounds of the present invention are accordingly useful in the prevention and treatment of a wide variety of inflammatory, infectious and immunoregulatory disorders and diseases. In addition, treatment of the aforementioned inflammatory, allergic and autoimmune diseases can also be contemplated for promoters of chemokine receptor function if one contemplates the delivery of sufficient compound to cause the loss of receptor expression on cells through the induction of chemokine receptor internalization or delivery of compound in a manner that results in the misdirection of the migration of cells.

In another aspect, the instant invention may be used to evaluate the putative specific agonists or antagonists of a G protein coupled receptor. The present invention is directed to the use of these compounds in the preparation and execution of screening assays for compounds that modulate the activity of chemokine receptors. Furthermore, the compounds of this invention are useful in establishing or determining the binding site of other compounds to chemokine receptors, e.g., by competitive inhibition or as a reference in an assay to compare its known activity to a compound with an unknown activity. When developing new assays or protocols, compounds according to the present invention could be used to test their effectiveness.

Specifically, such compounds may be provided in a commercial kit, for example, for use in pharmaceutical research involving the aforementioned diseases. The compounds of the instant invention are also useful for the evaluation of putative specific modulators of the chemokine receptors. In addition, one could utilize compounds of this invention to examine the specificity of G protein coupled receptors that are not thought to be chemokine receptors, either by serving as examples of compounds which do not bind or as structural variants of compounds active on these receptors which may help define specific sites of interaction.

The CCR-3 receptor binding test is based on a K562 cell line (leukemia myelogenic blast cells) transfected with the human chemokine receptor CCR-3 (hCCR-3-C1). The cell membranes were prepared by disrupting the hCCR-3 transfected K562 cells by nitrogen decomposition and centrifugation at 40000 g, 4° C. for 1 h. The membranes were re-suspended in the SPA incubation buffer without bovine serum albumin for storage in aliquots at −80° C.

The CCR-3 receptor binding assay with the radioligand $^{125}$Jodine-eotaxin-1 was performed in a Scintillation Proximity Assay (SPA) design. Cell membranes of hCCR-3 C1 cells were diluted in suitable concentrations (0.5-5 ug protein/well) in 96 well microtiter plates (1450-401, Wallac).

The test incubation mixture comprising 60 µl of the membrane suspension, 80 µl of the Wheat Germ Agglutinin coated PVT beads (organic scintillator, Amersham Pharmacia biotech) in a concentration of 0.4 mg and 40 µl of radiolabelled $^{125}$J rhEotaxin (Amersham, IM290) were incubated with 20 µl of the test compound (dissolved in DMSO dilutions) for 2 hours. The SPA incubation buffer contained 25 mM HEPES, 25 mM $MgCl_2$ $6 \times H_2O$, 1 mM $CaCl_2$ $2 \times H_2O$ and 0.1% bovine serum albumin. Included were controls for specific binding (no displacer added) and non-specific binding by adding unlabelled rhEotaxin (R&D Systems) or a test compound. Bound radioactivity was determined by scintillation counter (Micro Beta "Trilux", Wallac).

Determination of affinity of test compounds (dissociation constant $K_i$) was calculated by iterative fitting of experimental data using the law of mass action based program "easy sys" (Schittkowski, Num Math 68, 129-142 (1994)).

The utility of the compounds in accordance with the present invention as modulators of chemokine receptor activity may be demonstrated by methodology known in the art, such as the assays for CCR-2 and CCR-3 ligand binding, as disclosed by Ponath et al., J. Exp. Med., 183, 2437-2448 (1996) and Uguccioni et al., J. Clin. Invest., 100, 11371143 (1997). Cell lines for expressing the receptor of interest include those naturally expressing the chemokine receptor, such as EOL-3 or THP-1, those induced to express the chemokine receptor by the addition of chemical or protein agents, such as HL-60 or AML14.3D10 cells treated with, for example, butyric acid with interleukin-5 present, or a cell engineered to express a recombinant chemokine receptor, such as CHO or HEK-293. Finally, blood or tissue cells, for example human peripheral blood eosinophils, isolated using methods as described by Hansel et al., J. Immunol. Methods, 145, 105-110 (1991), can be utilized in such assays. In particular, the compounds of the present invention have activity in binding to the CCR-3 receptor in the aforementioned assays. As used herein, "activity" is intended to mean a compound demonstrating an IC50 of 10 MM or lower in concentration when measured in the aforementioned assays. Such a result is indicative of the intrinsic activity of the compounds as modulators of chemokine receptor activity.

Pharmaceutical Forms

The compounds are administered to a mammal in a therapeutically effective amount. By "therapeutically effective amount" it is meant an amount of a compound of formula 1a that, when administered alone or in combination with an additional therapeutic agent to a mammal, is effective to prevent or ameliorate diseases, wherein the activity of a CCR-3-receptor is involved, or the progression of this disease.

The compounds of this invention can be administered in such oral dosage forms as tablets, capsules (each of which includes sustained release or timed release formulations), pills, powders, granules, elixirs, tinctures, suspensions, syrups, and emulsions. They may also be administered in intravenous (bolus or infusion), intraperitoneal, subcutaneous, or intramuscular form, all using dosage forms well known to those of ordinary skill in the pharmaceutical arts. They can be administered alone, but generally will be administered with a pharmaceutical carrier selected on the basis of the chosen route of administration and standard pharmaceutical practice.

The dosage regimen for the compounds of the present invention will, of course, vary depending upon known factors, such as the pharmacodynamic characteristics of the particular agent and its mode and route of administration; the species, age, sex, health, medical condition, and weight of the recipient; the nature and extent of the symptoms; the kind of concurrent treatment; the frequency of treatment; the route of administration, the renal and hepatic function of the patient, and the effect desired. A physician or veterinarian can determine and prescribe the effective amount of the drug required to prevent, counter, or arrest the progress of the disorder.

By way of general guidance, the daily oral dosage of each active ingredient, when used for the indicated effects, will range between about 0.001 to 1000 mg/kg of body weight, preferably between about 0.01 to 100 mg/kg of body weight per day, and most preferably between about 1.0 to 20 mg/kg/day. Intravenously, the most preferred doses will range from about 1 to about 10 mg/kg/minute during a constant rate infusion. Compounds of this invention may be administered in a single daily dose, or the total daily dosage may be administered in divided doses of two, three, or four times daily.

Compounds of this invention can be administered in intranasal form via topical use of suitable intranasal vehicles, or via transdermale routes, using transdermale skin patches. When administered in the form of a transdermale delivery system, the dosage administration will, of course, be continuous rather than intermittent throughout the dosage regimen.

The compounds are typically administered in admixture with suitable pharmaceutical diluents, excipients, or carriers (collectively referred to herein as pharmaceutical carriers) suitably selected with respect to the intended form of administration, that is, oral tablets, capsules, elixirs, syrups and the like, and consistent with conventional pharmaceutical practices.

For instance, for oral administration in the form of a tablet or capsule, the active drug component can be combined with an oral, non-toxic, pharmaceutically acceptable, inert carrier such as lactose, starch, sucrose, glucose, methyl cellulose, magnesium stearate, dicalcium phosphate, calcium sulfate, mannitol, sorbitol and the like; for oral administration in liquid form, the oral drug components can be combined with any oral, non-toxic, pharmaceutically acceptable inert carrier such as ethanol, glycerol, water, and the like. Moreover, when desired or necessary, suitable binders, lubricants, disintegrating agents, and colouring agents can also be incorporated into the mixture. Suitable binders include starch, gelatine, natural sugars such as glucose or beta-lactose, corn sweeteners, natural and synthetic gums such as acacia, tragacanth, or sodium alginate, carboxymethylcellulose, polyethylene glycol, waxes, and the like. Lubricants used in these dosage forms include sodium oleate, sodium stearate, magnesium stearate, sodium benzoate, sodium acetate, sodium chloride, and the like. Disintegrators include, without limitation, starch, methyl cellulose, agar, bentonite, xanthan gum, and the like.

The compounds of the present invention can also be administered in the form of liposome delivery systems, such as small unilamellar vesicles, large unilamellar vesicles, and multilamellar vesicles. Liposomes can be formed from a variety of phospholipids, such as cholesterol, stearylamine, or phosphatidylcholines.

Compounds of the present invention may also be coupled with soluble polymers as targetable drug carriers. Such polymers can include polyvinylpyrrolidone, pyran copolymer, polyhydroxypropylmethacrylamide-phenol, polyhydroxyethylaspart-amidephenol, or polyethyleneoxidepolylysine substituted with palmitoyl residues.

Furthermore, the compounds of the present invention may be coupled to a class of biodegradable polymers useful in achieving controlled release of a drug, for example, polylactic acid, polyglycolic acid, copolymers of polylactic and polyglycolic acid, polyepsilon caprolactone, polyhydroxy butyric acid, polyorthoesters, polyacetals, polydihydropyrans, polycyanoacylates, and cross linked or amphipathic block copolymers of hydrogels.

Dosage forms (pharmaceutical compositions) suitable for administration may contain from about 1 milligram to about 100 milligrams of active ingredient per dosage unit.

In these pharmaceutical compositions the active ingredient will ordinarily be present in an amount of about 0.5-95% by weight based on the total weight of the composition.

Gelatine capsules may contain the active ingredient and powdered carriers, such as lactose, starch, cellulose derivatives, magnesium stearate, stearic acid, and the like. Similar diluents can be used to make compressed tablets. Both tablets and capsules can be manufactured as sustained release products to provide for continuous release of medication over a period of hours. Compressed tablets can be sugar coated or film coated to mask any unpleasant taste and protect the tablet from the atmosphere, or enteric coated for selective disintegration in the gastrointestinal tract.

Liquid dosage forms for oral administration can contain colouring and flavouring to increase patient acceptance.

In general, water, suitable oil, saline, aqueous dextrose (glucose), and related sugar solutions and glycols such as propylene glycol or polyethylene glycols are suitable carriers for parenteral solutions. Solutions for parenteral administration preferably contain a water soluble salt of the active ingredient, suitable stabilizing agents, and if necessary, buffer substances. Antioxidizing agents such as sodium bisulfite, sodium sulfite, or ascorbic acid, either alone or combined, are suitable stabilizing agents. Also used are citric acid and its salts and sodium EDTA. In addition, parenteral solutions can contain preservatives, such as benzalkonium chloride, methyl- or propyl-paraben, and chlorobutanol.

Suitable pharmaceutical carriers are described in Remington's Pharmaceutical Sciences, Mack Publishing Company, a standard reference text in this field.

Where two or more of the foregoing second therapeutic agents are administered with the compound of formula 1a, generally the amount of each component in a typical daily dosage and typical dosage form may be reduced relative to the usual dosage of the agent when administered alone, in view of the additive or synergistic effect of the therapeutic agents when administered in combination.

Particularly when provided as a single dosage unit, the potential exists for a chemical interaction between the combined active ingredients. For this reason, when the compound of formula 1a and a second therapeutic agent are combined in a single dosage unit they are formulated such that although the active ingredients are combined in a single dosage unit, the physical contact between the active ingredients is minimized (that is, reduced). For example, one active ingredient may be enteric coated. By enteric coating one of the active ingredients, it is possible not only to minimize the contact between the combined active ingredients, but also, it is possible to control the release of one of these components in the gastrointestinal tract such that one of these components is not released in the stomach but rather is released in the intestines. One of the active ingredients may also be coated with a material which effects a sustained-release throughout the gastrointestinal tract and also serves to minimize physical contact between the combined active ingredients.

Furthermore, the sustained-released component can be additionally enteric coated such that the release of this component occurs only in the intestine. Still another approach would involve the formulation of a combination product in which the one component is coated with a sustained and/or enteric release polymer, and the other component is also coated with a polymer such as a low viscosity grade of hydroxypropyl methylcellulose (HPMC) or other appropriate materials as known in the art, in order to further separate the active components. The polymer coating serves to form an additional barrier to interaction with the other component.

These as well as other ways of minimizing contact between the components of combination products of the present invention, whether administered in a single dosage form or administered in separate forms but at the same time by the same manner, will be readily apparent to those skilled in the art, once armed with the present disclosure.

What is claimed is:
1. A compound of general formula 1a,

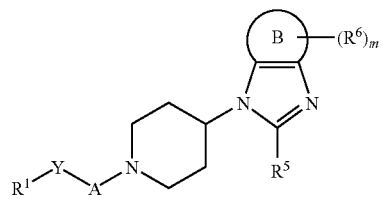

wherein
R$^1$ is phenyl, optionally substituted with one, two or three R$^2$;
R$^2$ are each independently —C$_{1-6}$-alkyl, —C$_{3-6}$-cycloalkyl, —C$_{1-6}$-haloalkyl, —C$_{1-6}$-aralkyl, halogen, —CN, —COOR$^3$, —COR$^3$, —CONR$^3$R$^4$, —NR$^3$R$^4$, —NR$^3$COR$^4$, —NR$^3$SO$_2$R$^4$, —OR$^3$, —NO$_2$, —SR$^3$, —SOR$^3$, —SO$_2$R$^3$ or —SO$_2$NR$^3$R$^4$;
R$^3$ is H or —C$_{1-6}$-alkyl;
R$^4$ is H or —C$_{1-6}$-alkyl;
R$^5$ is —C$_{1-6}$-alkyl
R$^6$ are each independently —C$_{1-6}$-alkyl, —C$_{1-6}$-alkoxy, —C$_{1-6}$-acyloxy, —C$_{1-6}$-aralkyl, —C$_{3-6}$-cycloalkyl, —C$_{1-6}$-haloalkyl, —C$_{1-6}$-thioalkyl, halogen, —OR$^3$, —SR$^3$, —CN, —NO$_2$, —COOR$^3$, —COR$^3$, —CONR$^3$R$^4$, —NR$^3$R$^4$, —NR$^3$COR$^4$, —NR$^3$SO$_2$R$^4$, —SOR$^3$, —SO$_2$R$^3$, —SO$_2$NR$^3$R$^4$, aryl or het;
A is —C$_{2-8}$-alkylene, optionally substituted with —C$_{1-3}$-alkyl, halogen or —OH;
B is aryl or het;
Y is —CF$_2$—, —NR$^4$—, —O—, —S(O)—;
n is 0, 1 or 2;
m is 0, 1, 2, 3 or 4;
and pharmaceutically acceptable salts thereof.

2. A compound according to claim 1, wherein R$^1$ and R$^5$ are defined as in claim 1 and
R$^2$ are each independently —C$_{1-6}$-alkyl, —C$_{1-6}$-haloalkyl, halogen, —CN, —OR$^3$ or —NO$_2$;
R$^3$ is H or —C$_{1-6}$-alkyl;
R$^6$ are each independently —C$_{1-6}$-alkyl, —C$_{1-6}$-alkoxy, —C$_{1-6}$-haloalkyl, halogen, —OR$^3$, —CN or —NO$_2$;
A is —C$_{2-8}$-alkylene;
B is aryl;
Y is —NH—, —O—, —S(O)$_n$—;
n is 0 or 2;
m is 0, 1 or 2;
and pharmaceutically acceptable salts thereof.

3. A compound of general formula 1b,

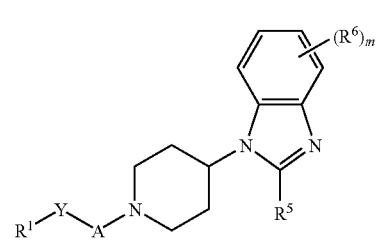

wherein R$^1$, R$^5$, R$^6$, A, Y and m are defined as in claim 1 or 2 and pharmaceutically acceptable salts thereof.

4. A compound according to any one of the claims 1-3 wherein,

Y is —NH—, —O—, —S(O)$_n$—;

A is —C$_{2-8}$-alkylene;

and pharmaceutically acceptable salts thereof.

5. A compound according to any one of the claims 1-4 wherein,

A is —CH$_2$—CH$_2$—CH$_2$—;

and pharmaceutically acceptable salts thereof.

6. A compound of general formula 1c,

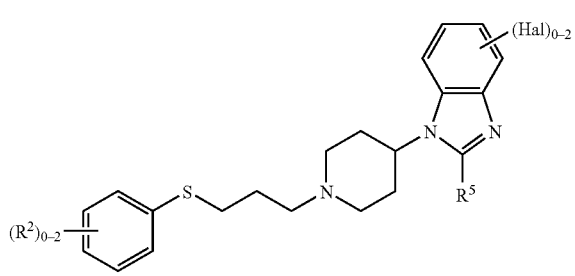

1c wherein R$^5$ is —C$_{1-6}$-alkyl and

R$^2$ is —CF$_3$ or halogen;

Hal is halogen;

and pharmaceutically acceptable salts thereof.

7. A compound of general formula 1d, and pharmaceutically acceptable salts thereof.

8. A pharmaceutical composition comprising one or more compounds of formula 1a, 1b, 1c or 1d according to one of claims 1-7 and a pharmaceutically acceptable carrier.

* * * * *